United States Patent [19]

Hirai et al.

[11] 4,186,269

[45] Jan. 29, 1980

[54] PROCESS FOR PRODUCING AN AROMATIC URETHANE

[75] Inventors: Yutaka Hirai; Katsuharu Miyate; Makoto Aiga, all of Omuta, Japan

[73] Assignee: Mitsui Toatsu Chemicals, Incorporated, Tokyo, Japan

[21] Appl. No.: 645,712

[22] Filed: Dec. 31, 1975

[30] Foreign Application Priority Data

Jan. 30, 1975 [JP] Japan ................................. 50-11891
Jul. 30, 1975 [JP] Japan ................................. 50-91987
Aug. 14, 1975 [JP] Japan ................................. 50-98081

[51] Int. Cl.² ........................................... C07C 125/06
[52] U.S. Cl. ................................. 560/25; 260/346.3; 544/37; 560/9; 560/12; 560/13; 560/22; 560/24; 560/26; 560/27; 560/28; 560/29; 560/30; 560/31; 560/32; 560/33; 544/322
[58] Field of Search ................. 260/471 C; 560/9, 12, 560/13, 24–33, 22

[56] References Cited

U.S. PATENT DOCUMENTS

3,454,620  7/1969  Gamlen et al. ................... 260/471 C

*Primary Examiner*—Vivian Garner
*Attorney, Agent, or Firm*—Fisher, Christen & Sabol

[57] ABSTRACT

An aromatic urethane is obtained at high yield without involving corrosion of a stainless steel reactor by interacting an aromatic nitro compound, an organic compound having at least one hydroxyl group therein and carbon monoxide in the presence of a catalyst composed of (1) palladium, ruthenium, rhodium or compounds thereof, (2) a Lewis acid, and (3) a tertiary amine. For instance, 2,4-dinitrotoluene, ethanol and carbon monoxide placed in a SUS-32 reactor are interacted in the presence of a catalyst composed of (1) 5% palladium on carbon, (2) ferric chloride, and (3) pyridine to obtain 2,4-diethyldicarbamatetoluene without corrosion of the reactor. After completion of the reaction, the catalyst and reaction product are separated from the reaction system; e.g., the insoluble catalyst is first separated and then the reaction solution is cooled down, e.g., to room temperature, to separate the reaction product as crystals, followed by separation of the crystals by filtration. Then, the reaction may be repeated by adding fresh 2,4-dinitrotoluene and ethanol and the separated catalyst to the resultant fitrate under pressurized conditions of a carbon monoxide atmosphere. By repeating the reaction in this manner, 2,4-diethyldicarbamatetoluene with a purity of 98% can be obtained at a yield of 90%.

9 Claims, No Drawings

PROCESS FOR PRODUCING AN AROMATIC URETHANE

BACKGROUND OF THE INVENTION

1. Field of the Invention

This invention relates to a process for the production of an aromatic urethane. More particularly, it relates to a process for the production of an aromatic urethane by interaction of an aromatic nitro compound, an organic compound having at least one hydroxyl group therein (hereinafter referred to as a hydroxyl group-containing organic compound) and carbon monoxide at elevated temperature under high pressure in the presence of a catalyst.

2. Description of the Prior Art

In most cases, urethanes have been produced by the reaction of isocyanates and hydroxyl group-containing organic compounds. In recent years, there have been developed many novel processes for producing urethanes partly due to shortages and rising costs of starting materials for producing isocyanates and partly due to the strong toxicity of intermediates. However, the newly developed processes still have several problems to be solved and, therefore, are not put into practice for production on an industrial scale.

For example, U.S. Pat. No. 3,338,956 describes a process for producing an aromatic urethane from an alcohol, carbon monoxide and an aromatic nitro compound in the presence of rhodium chlorocarbonyl. However, this process is not economically advantageous in efficiently obtaining highly pure aromatic urethane since the yield is low even though the reaction is effected over a long period of time in the presence of a large quantity of catlyst.

Further, German Pat. No. 1,543,051 teaches a process for producing an aromatic urethane wherein a hydroxyl group-containing organic compound, carbon monoxide and a nitro compound are interacted in the presence of a catalyst of a carbonyl group-containing derivative of a metal of group VIII of the Periodic Table in coexistence with a promoter composed of a salt of a metal selected from metals capable of existing in two or more valence states. However, this process is of little industrial practical value since the yield of product is low even when a mononitro organic compound is used as starting material and becomes lower when a dinitro compound is used.

Further, U.S. Pat. No. 3,531,512 describes a process using a catalyst of palladium and a Lewis acid in which the yield of urethane reaches as high as 80%–90% under certain conditions even when a dinitro compound is employed as starting material. In order to attain such high yield, however, it is essential to effect the urethanation reaction under such severe conditions as a carbon monoxide initial pressure of 190–350 kg/cm$^2$ and a reaction temperature of 190°–200° C. In addition, the process has a vital disadvantage from an industrial viewpoint in that the Lewis acid, e.g., ferric chloride, used as a promoter materially attacks a metal such as stainless steel by its corrosive action. Accordingly, to put this process into practice on an industrial scale requires use of a glass or tantalum reactor. However, the use of glass or tantalum in such high temperature and high pressure reactions involves several technical and economical disadvantages.

Moreover, there is described in French Pat. No. 2,197,862 a process using as catalyst selenium, sulfur or a compound thereof and a base or water. This process is advantageous in that the reaction conditions are milder than those of other processes which have been known to date and that the yield of urethane is relatively high, but disadvantageous in that amines are secondarily produced. By this process, a urethane with high purity is difficult to obtain since the urethane product is readily contaminated with the secondarily produced amines and the selenium or sulfur used as catalyst.

SUMMARY OF THE INVENTION

In view of the above difficulties, it is a primary object of the present invention to provide a process for producing an aromatic urethane whereby the aromatic urethane product can be obtained at high yield under temperature and pressure conditions far milder than those of conventional processes.

It is a further object of the present invention to provide a process for producing an aromatic urethane which is free from corrosion of a reactor.

It is another object of the present invention to provide a process for producing an aromatic urethane in which it is possible to recover the catalyst from the reaction system.

It is a still further object of the present invention to provide a process for producing an aromatic urethane in which the catalyst and the reaction mother liquor are repeatedly employed, thereby increasing the production quantity of the aromatic urethane per unit quantity of catalyst to a considerable extent.

According to the present invention, there is provided a process for producing an aromatic urethane which comprises interacting an aromatic nitro compound, a hydroxyl group-containing organic compound and carbon monoxide in the presence of a catalyst composed of (1) palladium, ruthenium, rhodium or compounds thereof, (2) a Lewis acid, and (3) a tertiary amine. Owing to inclusion of the tertiary amine, the degree of corrosion of the reactor is suppressed to below 0.05 mm./year with regard to stainless steel, allowing use of stainless steel as a reactor material. The palladium, ruthenium or rhodium catalyst which has been considered difficult to recover in conventional processes due to dissolution thereof in the reaction solution can be readily recovered in the process of the present invention at high yield in the form of a solid, due also to inclusion of the tertiary amine in the catalyst. Further, the process of the invention permits production of a desired aromatic urethane at high yield at reaction temperatures and pressures much lower than those of known processes, especially when a nitrogen-containing heterocyclic tertiary amine is employed as the tertiary amine. In other words, the reaction velocity in the process of the present invention is much higher than those of conventional processes when compared under the same reaction conditions. Thus, the process of the present invention is conveniently feasible from an industrial point of view. Further, with a nitrogen-containing heterocyclic tertiary amine being used as the tertiary amine, the reaction mother liquor which is obtained, after completion of the reaction, by separating the insoluble catalyst and the precipitated or crystallized urethane from the reaction solution, or both the reaction mother liquor and the recovered catalyst can be reused by recirculation into the reaction system. When, in conventional processes, a catalyst and/or reaction mother liquor which has been separated from the reaction solution obtained after completion of the reaction is reused for further reaction of fresh aromatic nitro compound, the reaction proceeds only very slowly, so that most of the nitro compound remains unreacted or in an intermediate stage, or a large amount of tar-like by-product is formed, lowering the yield and purity of the final urethane product and making it almost impossible to reuse the resultant mother liquor by recirculation. Under these circumstances, it is common practice in the conventional processes to discharge all of the reaction solution from the reactor for separating catalyst, solvent and reaction product from each other by suitable procedures. Then, fresh solvent and catalyst must be charged into the reactor for commencement of further reaction. In known processes, only a small amount of catalyst can be directly recovered from a reaction solution in the form of a solid. A major portion of the catalyst is dissolved in the reaction solution and it is very difficult to economically collect catalytic components from the reaction solution and to regenerate the same in the form of a highly active fresh catalyst.

By the present invention, the recovery of catalyst for reuse and the repeated use of reaction mother liquor, which have been difficult in known processes, have now become possible. As a consequence, the amount of starting aromatic nitro compound to be treated per unit quantity of catalyst is increased by far in comparison with known processes, the process of the invention industrially showing a distinct advantage from an economical point of view. The repeated use of the reaction mother liquor by recirculation makes it possible to reutilize reaction intermediates in a very efficient way, resulting in production of an aromatic urethane of high purity at high yield.

DESCRIPTION OF THE PREFERRED EMBODIMENTS

The starting aromatic nitro compounds may be mononitro compounds or polynitro compounds including, for example, nitrobenzene, dinitrobenzenes, dinitrotoluenes, nitronaphthalenes, nitroanthracenes, nitrobiphenyls, bis(nitrophenyl)alkanes, bis(nitrophenyl) ethers, bis(nitrophenyl)thioethers, bis(nitrophenyl) sulfons, nitrodiphenoxyalkanes, and heterocyclic compounds such as nitrophenothiazines and 5-nitropyrimidine. Typical of the aromatic nitro compounds are nitrobenzene, o-, m- or p-nitrotoluene, o-nitro-p-xylene, 1-nitronaphthalene, m- or p-dinitrobenzene, 2,4-or 2,6-dinitrotoluene, dinitromesitylene, 4,4'-dinitrobiphenyl, 2,4-dinitrobiphenyl, 4,4'-dinitrodibenzyl, bis(4-nitrophenyl)methane, bis(4-nitrophenyl)ether, bis(2,4-dinitrophenyl)ether, bis(4-nitrophenyl)thioether, bis(4-nitrophenyl)sulfon, bis(4-nitrophenoxy)ethane, $\alpha,\alpha'$-dinitro-p-xylene, $\alpha,\alpha'$-dinitro-m-xylene, 2,4,6-trinitrotoluene, o-, m-, or p-chloronitrobenzene, 1-chloro-2,4-dinitrobenzene, 1-bromo-4-nitrobenzene, 1-fluoro-2,4-dinitrobenzene, o-, m- or p-nitrophenylcarbamate, o-, m- or p-nitroanisole, 2,4-dinitrophenetole, m-nitrobenzaldehyde, p-nitrobenzoyl chloride, ethyl-p-nitrobenzoate, m-nitrobenzenesulfonyl chloride, 3-nitrophthalic anhydride, 3,3'-dimethyl-4,4'-dinitrobiphenyl, 1,5-dinitronaphthalene and the like. These aromatic nitro compounds may be used singly or in combination. Further, isomers and homologues of these compounds may be also employed. Of these, 2,4-dinitrotoluene and 2,6-dinitrotoluene are most preferred since the isocyanates obtained by thermal decomposition of aromatic urethanes prepared from these dinitrotoluenes in accordance with the process of the invention are industrially useful.

The hydroxyl group-containing organic compounds useful in the process of the invention include monohydric alcohols having a primary, secondary or tertiary hydroxyl group, polyhydric alcohols, monohydric phenols and polyhydric phenols. The alcohols include linear or branched alkyl alcohols, cycloalkyl alcohols, alkylene alcohols, cycloalkylene alcohols, aralkyl alcohols and the like, each in the monohydric or polyhydric form. These alcohols may contain therein a substituent containing oxygen, nitrogen, sulfur or a halogen atom, such as a halogen, sulfoxide,, sulfon, amine, amide, carbonyl or carboxylic acid ester group. Examples of the alcohols are monohydric alcohols such as methyl alcohol, ethyl alcohol, n- or iso-propyl alcohol, n-, iso- or t-butyl alcohol, linear or branched amyl alcohol, hexyl alcohol, cyclohexyl alcohol, lauryl alcohol, cetyl alcohol, benzyl alcohol, chlorobenzyl alcohol, methoxybenzyl alcohol and the like, dihydric alcohols such as ethylene glycol, diethylene glycol, propylene glycol, dipropylene glycol and the like, trihydric alcohols such as glycerine, hexanetriol and the like, and more functional polyols. Of these, ethyl alcohol is most preferred from the practical point that the aromatic urethane obtained therefrom in accordance with the process of the invention can be thermally decomposed to give an isocyanate.

The phenols useful in the present invention include, for example, phenol, chlorophenol, cresol, ethylphenol, linear or branched propylphenol, butyl or higher alkylphenols, catechol, resorcin, 4,4'-dihydroxydiphenylmethane, 2,2'-isopropylidenediphenol, anthranol, phenanthrol, pyrogallol, fluoroglucinol and the like.

The amount of the hydroxyl group-containing organic compound may be greater than theoretical, i.e., equivalent to the nitro groups of the aromatic nitro compound. In the usual case, the hydroxyl group-containing organic compound is preferably employed in excess.

The primal catalyst used in the reaction of the invention is a simple substance such as palladium, rhodium or ruthenium, or a catalytically active compound thereof. Examples of the catalytically active compounds are the halides, cyanides, thiocyanides, isocyanides, oxides, sulfates, nitrates and carbonyl compounds of the above metals, and complex salts of the halides and either tertiary amines such as triethylamine, pyridine, isoquinoline and the like, or organic phosphorous compounds such as triphenylphosphine and the like.

Representative of these complex salts are complexes of halides and pyridine such as Pd(pyridine)$_2$Cl$_2$, Pd(pyridine)$_2$Cl$_4$, Rh(pyridine)$_3$Cl$_3$, Ru(pyridine)$_2$Cl$_4$, [Ru(pyridine)$_4$Cl$_2$]Cl and the like, complexes of halides and isoquinoline in which pyridine is replaced by isoquinoline in the above-described complexes, complexes of halides and triphenylphosphine such as Pd(triphenylphosphine)$_2$Cl$_2$ and complexes of halides and triethylamine such as Pd(triethylamine)$_2$Cl$_2$. It should be noted that the nitrogen-containing heterocyclic compound such as pyridine which is employed as one component of the complex salt is considered to be part of the nitrogen-containing heterocyclic tertiary amine required for constituting the catalytic system in the process of the invention, as will be described more in detail hereinafter.

These primal catalysts may be used as such in the urethanation reaction or may be supported on inert carriers such as alumina, silica, carbon, barium sulfate, calcium carbonate, asbestos, bentonite, diatomaceous earth, Fuller's earth, an organic ionexchange resin, magnesium silicate, aluminum silicate, Molecular Sieves, and the like. In this connection, the carriers may be placed in a reactor independently of the primal catalyst such as palladium, rhodium, ruthenium or compound thereof. The weight ratio of the primal catalyst to the starting aromatic nitro compound is generally $1-1\times10^{-5}$, preferably $5\times10^{-1}-1\times10^{-4}$, when the primal catalyst is expressed in terms of the simple metal substance.

In the present invention, the Lewis acid is employed as a promoter. The Lewis acids useful in the present invention are those described in "Physical Organic Chemistry", 1962, by Jack Hine and published by McGraw Hill Book Co., New York, including Bronsted acids. The Lewis acids are halides, sulfates, acetates, phosphates and nitrates of the metals tin, titanium, germanium, aluminum, iron, copper, nickel, zinc, cobalt, manganese and the like, and include, for example, ferric chloride, ferrous chloride, stannic chloride, stannous chloride, aluminum chloride, cupric chloride, cuprous chloride, copper acetate, and the like. Of these, ferric chloride is preferred. The weight ratio of the Lewis acid to the starting aromatic nitro compound is generally in the range of $2-2\times10^{-3}$, preferably $1-5\times10^{-2}$.

Broadly, the tertiary amines suitable for the practice of the present invention are aliphatic tertiary amines, alicyclic tertiary amines, aromatic tertiary amines, heterocyclic tertiary amines, N,N-dialkylaromatic amines, N,N-dicycloalkyl aromatic amines and N-alkyl-N-cycloalkyl aromatic amines. These tertiary amines may contain therein a substituent which does not take part in or is inert to the urethanation reaction of the invention and which includes, for example, a halogen atom, alkyl group, aryl group, alkenyl group, cyano group, aldehyde group, alkoxy group, phenoxy group, thioalkoxy group, thiophenoxy group, carbamyl group, carboalkoxy group, thiocarbamyl group or the like. Examples of the tertiary amines include aliphatic tertiary amines such as trimethylamine, triethylamine, tripropylamine, tributylamine, etc., alicyclic tertiary amines such as N,N-dimethylcyclohexylamine, N,N-diethylcyclohexylamine, N,N-diisopropylcyclohexylamine, 1,4-diazabicyclo[2,2,2]octane and the like, aromatic tertiary amines such as triphenylamine, etc., nitrogen-containing heterocyclic tertiary amines such as pyridine, quinoline, isoquinoline, etc., N,N-dimethylaniline, N,N-diethylaniline, N,N-diisopropylaniline, etc. Use of the nitrogen-containing heterocyclic tertiary amines results in most remarkable improvements in the yield of urethane and in the reaction velocity. As described hereinbefore, when the nitrogen-containing heterocyclic tertiary amine is employed in the reaction, either the reaction mother liquor alone which is obtained, after completion of the reaction, by separating the insoluble catalyst and precipitated urethane from the reaction solution, or both the mother liquor and the separated catalyst may be recirculated to the reaction system for reuse.

Further examples of the nitrogen-containing heterocyclic tertiary amines useful in the process of the invention include 1-methylpyrrole, 1-phenylpyrrole, 1-methylimidazole, 1-methylindole, 1-phenylindole, indolenine, 2-isobenzazole, indolizine, 1-methylcarbazole, 2-chloropyridine, 2-bromopyridine, 2-fluoropyridine, 4-phenylpyridine, 2-methylpyridine, 2-methyl-5-ethylpyridine, 2,6-dimethylpyridine, 2,4,6-trimethylpyridine, 2-vinylpyridine, 2-styrylpyridine, 3-chloropyridine, 2,6-dichloropyridine, 2-chloro-4-methylpyridine, 4-phenylthiopyridine, 2-methoxypyridine, 4-dimethylaminopyridine, $\alpha$-picolinic acid phenyl ester, $\gamma$-picolinic acid methyl ester, 2,6-dicyanopyridine, $\alpha$-picolinic aldehyde, $\alpha$-picolinic amide, 5,6,7,8-tetrahydroquinoline, 2,2-dipyridyl, 2-chloroquinoline, acridine, phenanthridine, benzoquinoline, benzoisoquinoline, naphthyridine, pyrazine, 4,6-dimethylpyrazine, 2,6-dimethylpyrazine, pyridazine, pyrimidine, quinoxaline, 2,3-di-methylquinoxaline, quinazoline, phthalazine, phenazine, cinnoline, pteridine, and the like, and they may be used in the form of polymers such as polyvinyl pyridine. In addition, simple salts of the nitrogen-containing heterocyclic tertiary amines may be also employed including the nitrates, hydrohalogenic acid salts, sulfates, acetates and the like. Moreover, quaternary salts of nitrogen-containing heterocyclic compounds and oxides of nitrogen-containing heterocyclic tertiary amines may be also employed.

The tertiary amines may be introduced into the reactor independently of the starting materials and the other catalytic components or may be mixed with part of the other catalytic components for conversion thereof to an appropriate compound such as a complex or an addition product. It is well known that nitrogen-containing heterocyclic tertiary amines and a compound of palladium, ruthenium or rhodium form complex salts as described in Gmerins Handbuch der Anorganischen Chemie', Ser. No. 63-67. That is, various complex salts of nitrogen-containing heterocyclic tertiary amines such as pyridine, quinoline, isoquinoline and the like and of the halides, cyanides, thiocyanides, and isocyanides of palladium, ruthenium and rhodium are known. For example, palladium chloridepyridine complex expressed as $PdCl_2(pyridine)_2$ which has been previously prepared may be used without independently introducing pyridine and palladium chloride into the reactor. Further, it is also well known that nitrogen-containing heterocyclic tertiary amines form complex salts in combination with Lewis acids including, for example, a complex of pyridine and ferric chloride or ferrous chloride expressed by the formulas $FeCl_3(C_5H_5N)_3$, $FeCl_3(C_5H_5N)_4$ and $FeCl_2(C_5H_5N)_3$, a complex of germanium chloride and pyridine expressed by the formula $GeCl_4(C_5H_5N)_3$, and complexes of the above-mentioned formulae in which pyridine is substituted by quinoline or isoquinoline. These complex compounds which have been previously prepared may also be employed in the present invention without independently adding a nitrogen-containing heterocyclic tertiary amine and a Lewis acid to the reaction system.

These complex compounds can be obtained by a conventional preparation method. That is, a complex compound is readily formed by adding the complex ingredients with agitation to a suitable solvent such as benzene, monochlorobenzene dichlorobenzene or ethanol or to an excess of the nitrogen-containing heterocyclic tertiary amine. In the formation, it is desirable to remove moisture from the employed solvent and the complex ingredients as far as possible. In some cases, complex compounds with higher activity are obtained when the formation treatment of the complex compounds is effected in an atmosphere of carbon monoxide. The complex compounds thus obtained may be used in the urethanation reaction after isolation thereof from the solvent used or from the excess of nitrogen-containing heterocyclic tertiary amine by distillation, or may be used as such together with the solvent employed or with the excess of nitrogen-containing heterocyclic tertiary amine.

The tertiary amine added to the reaction system of the present invention serves to suppress corrosion of the reactor material by the Lewis acid. The molar ratio of tertiary amine to the anions of the Lewis acid is generally in the range of 0.5 to 5, and preferably is equivalent thereto. The amount of tertiary amine corresponding to, for example, a 0.5 molar ratio to the anions of the Lewis acid such as, for example, $FeCl_2$ is, thus, 2 anions/mole of $FeCl_2 \times 0.5 = 1$ mole of the tertiary amine. Similarily, when $FeCl_3$ is used as the Lewis acid, the corresponding amount is 3 anions/mole of $FeCl_3 \times 0.5 = 1.5$ moles of the tertiary amine. When a tertiary amine is used in a molar ratio of less than 0.5, corrosion is suppressed to some extent but the suppressing effect will be accordingly diminished. On the other hand, the tertiary amine may be employed in a molar ratio of greater than 5 since the suppression effect becomes greater with a greater mole ratio. However, the reaction velocity and the yield remain substantially unchanged even though the tertiary amine is employed in a molar ratio greater than 5, such an excess being unnecessary in the general case. It will be noted that tertiary amines give a most pronounced corrosion-suppression effect when the reaction system contains little or no water.

In the reaction of the present invention, the catalytic components are primarily deposited in the form of solids after completion of the reaction due to presence of the tertiary amine, it thus being possible to separate and collect the solid catalyst from the reaction solution. The structural form of the thus collected catalyst is not presently known, but it has been found that it may be reused as it is or after treatment by a suitable method such as washing with a solvent.

In the process of the invention, although no specific solvent is required to be added to the reaction system since the hydroxyl group-containing organic compound serves as solvent, a solvent may be used. Examples of the solvent include aromatic solvents such as benzene, toluene, xylene, and the like, nitriles such as acetonitrile, benzonitrile and the like, sulfones such as sulfolane and the like, aliphatic halogenated hydrocarbons such as 1,1,2-trichloro-1,2,2-trifluoroethane and the like, halogenated aromatic hydrocarbons such as monochlorobenzene, dichlorobenzene, trichlorobenzene and the like, ketones, esters, tetrahydrofuran, 1,4-dioxane, 1,2-dimethoxyethane, and the like.

Although the manner of charging the starting materials is not particularly limited, it is desirable that all or part of the aromatic nitro compound and the Lewis acid is dissolved in the hydroxyl group-containing organic compound or a suitable solvent and then added to the reaction system. The order of addition of the starting materials also is not limited and may be arbitrarily changed within the limitations of the apparatus used. For instance, a hydroxyl group-containing compound, catalytic components, tertiary amine and aromatic nitro compound may be introduced altogether into a suitable pressure-resistant reactor such as an autoclave, into which carbon monoxide is further fed under pressure, followed by heating under agitating conditions until the reaction is complete. Carbon dioxide which is formed during the reaction is exhausted by any suitable means, and the carbon monoxide may be fed either intermittently or continuously. The reaction may be effected by a batchwise, semi-continuous or continuous method under urethanation conditions. The reaction is generally effected under an initial carbon monoxide pressure of 10 kg/cm$^2$–500 kg/cm$^2$. The reaction temperature is generally in the range of 80° to 260° C., preferably from 140° to 200° C. The reaction proceeds more rapidly at higher temperatures. When the concentration of aromatic nitro compound is high and is likely to be decomposed during the reaction, the reaction may be carried out, as described in German Pat. No. 1,924,429, by a two-stage process, the first stage reaction being effected in the vicinity of 160° C. and the second stage reaction in the vicinity of 190° C. In this connection, however, the use of a nitrogen-containing heterocyclic tertiary amine as the tertiary amine component ensures that the reaction will proceed very rapidly even at a temperature of 140° to 160° C. and avoid the problem of decomposition.

The reaction time varies depending upon the property of the nitro compound, reaction temperature and pressure, kind and amount of catalyst, and kind and type of reaction apparatus and it is generally in the range of 5 minutes to 6 hours.

After completion of the reaction, the reaction mixture is cooled and the gases in the reactor are evacuated therefrom. Then, the thus cooled reaction mixture is subjected to filtration, distillation or other suitable separation treatments for separating the produced urethane from unreacted materials, by-products, solvent and catalyst. The most ordinary aftertreatment procedure is as follows. The reaction solution obtained after completion of the reaction is cooled and the gases are evacuated from the reactor. Then, the insoluble catalyst is removed from the reaction solution by a suitable method such as filtration or centrifugal separation. The resultant filtrate is further cooled sufficiently to separate the aromatic urethane as crystals. Alternatively, the reaction solution may be first cooled to an extent sufficient to separate both catalyst and urethane therefrom. Then, the separated mixture is introduced into a solvent capable of selectively dissolving the urethane alone therein to further separate the urethane from the catalyst. Solvents useful for this purpose include, for example, methanol, ethanol, benzene, toluene, chloroform and the like.

In cases where a nitrogen-containing heterocyclic tertiary amine is used as the tertiary amine, the reaction mother liquor which is obtained by separating the catalyst and urethane product from the reaction solution and which still contains small amounts of catalyst, urethane and by-products may be reused together with the recovered catalyst in a later cycle of reaction. Use of fresh catalyst instead of the recovered catalyst is uneconomical since the recovered one exhibits a satisfactory high catalytic activity. A later reaction using the reaction mother liquor fed by recirculation may be effected, similarly as in the initial case, by adding to the mother liquor an aromatic nitro compound, a hydroxyl group-containing compound and the recovered catalyst. Fresh catalyst may also be added to the reaction solution, if necessary. Fresh catalyst is not necessarily required to be added to the reaction system after every reaction cycle and may be added only when the reaction proceeds slowly after several cycles have been repeatedly carried out without addition of fresh catalyst. In order to accelerate the reaction velocity, it is generally more effective to add the Lewis acid and nitrogen-containing heterocyclic tertiary amine rather than the noble metal component such as palladium, ruthenium or rhodium.

The amount of fresh catalyst to be added is changed with the degree of reduction of the reaction velocity, kinds of starting materials and manner of reaction. In general, however, the amount is in the range of 5%–100% of that employed in the initial reaction cycle.

The aromatic urethane produced by the process of the invention has a diversity of applications as starting material for agricultural chemicals, isocyanates and polyurethanes.

The present invention will be more particularly illustrated by way of the following examples, which should not be construed as limiting the present invention thereto. In the examples, the reactions were effected in a stainless steel (SUS 32) autoclave equipped with an electromagnetic agitator and the degree of corrosion of material was determined from weight loss and surface area of agitating blades (made of SUS 32). The conversion and yield in the examples were calculated on the basis of the results of gas chromatography and liquid chromatography.

EXAMPLE 1

8.0 Grams of nitrobenzene, 1.6 grams of ferric chloride and 2.4 grams of pyridine were dissolved in ethanol, respectively. The resultant solutions were placed in a 500 ml. autoclave together with 0.5 gram of a commercially available 5% palladium on carbon catalyst, to which was further added ethanol to make the total amount 200 ml. The ethanol used was first subjected to a dehydration treatment using magnesium ethoxide to reduce the water content to below 0.01%, and this was repeated in all of the following examples.

The air in the autoclave was replaced by nitrogen gas and then carbon monoxide was fed into the autoclave until its initial pressure reached 120 kg/cm$^2$. The reaction was carried out at 190° C. for 1 hour with agitation. After completion of the reaction, the reaction system was cooled to 50° to 60° C. and the gases were exhausted from the autoclave. Then, the reaction solution was subjected to filtration for separation of solids therefrom. The ethanol was removed by distillation from the filtrate to obtain a reaction product. As a result of the chromatographic analyses of the reaction product, it was found that N-phenylcarbamic acid ethyl ester was obtained at a yield of 92%. The degree of corrosion of the agitating blades was found to be 0.030 mm./year, showing substantially no change on the surfaces of the blades.

COMPARATIVE EXAMPLE 1

Example 1 was repeated with the exception that the pyridine was omitted. As a result, the yield was 85% and the degree of corrosion of the agitating blades was 1.50 mm./year, pittings being observed on surfaces of the blades.

EXAMPLE 2

10.7 Grams of 2,4-dinitrotoluene, 1.6 grams of ferric chloride and 2.4 grams of pyridine which had been dissolved in ethanol, respectively, were introduced into a 500 ml. autoclave to which was first added 0.5 gram of 5% palladium on carbon and then ethanol to make the total amount 200 ml. Thereafter, carbon monoxide was fed to an initial pressure of 120 kg/cm$^2$ at room temperature. The reaction system was heated to 160° C. with agitation and maintained at the same temperature for 60 minutes followed by further heating up to 190° C. and holding at that temperature for 60 minutes.

Then, the reaction system was cooled down to 50°–60° C. and the gases in the autoclave were exhausted from the reaction system. The solids were removed by filtration. Analysis of the catalyst in the solid material by means of an atomic absorption spectrometer revealed that the catalyst was recovered in an amount of 85% on the basis of that charged. The filtrate was treated in the same manner as in Example 1 to obtain the urethane product. Chromatographic analyses of the product revealed that the conversion of 2,4-dinitrotoluene was 100% and that the yield of diethyltoluene-2,4-dicarbamate (hereinafter referred to simply as diurethane) was 67% and that of mononitrotoluenemonoethylcarbamate (hereinafter referred to as mononitromonourethane) was 25%, the total yield thereof reaching 92%. Further, the degree of corrosion of the agitating blades was found to be 0.018 mm./year.

COMPARATIVE EXAMPLE 2

Example 2 was repeated with the exception that the pyridine was omitted. The reaction proceeded more slowly than that of Example 2 and the catalyst recovered in the form of a solid was 14% of that initially charged. Chromatographic analyses of the resultant product revealed that the conversion of 2,4-dinitrotoluene was 100%, that the yield of the diurethane was 30% and that of the mononitromonourethane was 50%, with a total yield of 80%. The degree of corrosion of the agitating blades was 2.31 mm./year, a number of pits being observed on the surfaces of the blades.

EXAMPLE 3

Example 2 was repeated except that 3.5 grams of pyridine was used and the reaction was effected under a carbon monoxide initial pressure of 200 kg/cm$^2$ at 190° C. for 2 hours. The conversion of 2,4-dinitrotoluene was 100%. The yield of the diurethane was 82% and that of the mononitromonourethane was 1%. Further, the degree of corrosion of the blades was 0.004 mm./year.

EXAMPLES 4–11

Example 2 was repeated except that such catalysts, organic nitro compounds, hydroxyl group-containing organic compounds and reaction conditions as indicated in Table 1 were used. In all of Examples 4–11, the reactants used were 10.7 grams of 2,4-dinitrotoluene, 200 ml. of hydroxyl group-containing organic compound and 1.6 grams of ferric chloride.

Table 1

| Example No. | Hydroxyl group containing organic compound | Primal catalyst Kind | Amount (g.) | Tertiary amine Kind | Amount (g.) | CO initial pressure (Kg/cm$^2$G) |
|---|---|---|---|---|---|---|
| 4 | Ethanol | 5% Pd on carbon | 0.5 | Isoquinoline | 5.6 | 70 |
| 5 | Ethanol | 5% Pd on carbon | 0.5 | Triethylamine | 2.8 | 70 |
| 6 | Ethanol | 5% Pd on carbon | 0.5 | DABCO[1] | 2.6 | 120 |
| 7 | Ethanol | 5% Pd on carbon | 0.5 | Dimethylaniline | 3.6 | 120 |
| 8 | Ethanol | 5% Ru on carbon | 0.6 | Pyridine | 2.4 | 120 |

Table 1-continued

| | | | | | | |
|---|---|---|---|---|---|---|
| 9 | Ethanol | 1% Rh on alumina | 3.0 | Pyridine | 2.4 | 120 |
| 10 | Ethanol | PdCl$_2$ | 0.012 | Pyridine | 2.4 | 70 |
| 11 | Phenol | 5% Pd on carbon | 0.5 | Pyridine | 2.4 | 140 |

| Example No. | Reaction temperature/ reaction time (°C./hr) | Degree of corrosion (mm./year) | Conversion of nitro compound (%) | Yield Mononitromono- urethane (%) | Diurethane (%) |
|---|---|---|---|---|---|
| 4 | 160/1.5 + 190/1 | 0.015 | 95 | 20 | 60 |
| 5 | 190/2 | 0.001 | 96 | 15 | 47 |
| 6 | 160/1 + 190/1 | 0.014 | 67 | 12 | 35 |
| 7 | 160/1 + 190/1.5 | 0.060 | 97 | 21 | 54 |
| 8 | 160/1 + 190/1 | 0.012 | 51 | 33 | 8 |
| 9 | 160/1 + 190/1 | 0.010 | 48 | 29 | 11 |
| 10 | 160/1.5 + 190/1.5 | 0.047 | 100 | 33 | 49 |
| 11 | 160/1 + 190/1 | 0.013 | 98 | 17 | 71 |

[1] 1,4-diazabicyclo [2,2,2] octane

EXAMPLE 12

18.2 Grams of 2,4-dinitrotoluene, 150 ml. of ethanol, 1.56 grams of 5% Pd on alumina, 4.2 grams of ferric chloride and 6.3 grams of pyridine were used for reaction in the same manner as in Example 2 under an initial carbon monoxide pressure of 70 kg/cm$^2$G at a reaction temperature of 160° C. for 150 minutes. About 80% of the catalyst was recovered from the solids obtained from the reaction solution. Analyses of the reaction solution revealed that it was substantially free of starting 2,4-dinitrotoluene and intermediate of mononitromonourethane and that the yield of the diurethane was 95%. The degree of corrosion of the agitating blades was as small as 0.01 mm./year.

Then, 14.5 grams of 2,4-dinitrotoluene, 120 ml. of ethanol and 8.0 grams of the recovered catalyst were used for reaction under an initial carbon monoxide pressure of 70 kg/cm$^2$G at a reaction temperature of 160° C. for 150 minutes. The solid catalyst was recovered from the reaction solution obtained after completion of the reaction in the amount of 7.0 grams. The reaction solution was subjected to chromatographic analyses, revealing that the yield of diurethane was 95%.

COMPARATIVE EXAMPLE 3

Example 12 was repeated with the exception that the pyridine was omitted. The reaction was complete 200 minutes after commencement thereof. Chromatographic analyses revealed that the product contained no 2,4-dinitrotoluene, 10% of mononitromonourethane and that the yield of the diurethane was 60%. The degree of corrosion of the agitating blades was as great as 3.5 mm./year. Only a small amount of the catalyst was recovered in the form of a solid.

EXAMPLE 13

The reaction was conducted in the same manner as in Example 12 using 10.3 grams of isoquinoline instead of 6.3 grams of pyridine. 150 Minutes after commencement of the reaction, the diurethane was obtained at a yield of 94%.

EXAMPLE 14

The reaction was conducted in the same manner as in Example 12 using 7.4 grams of picoline instead of 6.3 grams of pyridine. 230 Minutes after commencement of the reaction, the mononitromonourethane and diurethane were obtained at yields of 8% and 82%, respectively.

EXAMPLE 15

Example 12 was repeated using 7.6 grams of ferric bromide instead of 4.2 grams of ferric chloride thereby to obtain the diurethane at a yield of 85%.

EXAMPLE 16

Example 12 was repeated using 8.0 grams of ferrous iodide instead of 4.2 grams of ferric chloride to obtain the diurethane at a yield of 83%.

EXAMPLE 17

Example 12 was repeated using 3.5 grams of aluminum chloride instead of 4.2 grams of ferric chloride. 200 Minutes after commencement of the reaction, the diurethane was obtained at a yield of 77%.

EXAMPLE 18

Example 17 was repeated using 6.7 grams of stannic chloride instead of 4.2 grams of aluminum chloride. Similar results were obtained.

EXAMPLE 19

Example 17 was repeated using 3.5 grams of cupric chloride instead of 4.2 grams of aluminum chloride to obtain the diurethane at a yield of 82%.

EXAMPLES 20-23

Example 12 was repeated using 5% Pd on carbon (Example 20), palladium chloride (Examples 21 and 22), and a palladium chloride-pyridine complex (Example 23), respectively, instead of 5% Pd on alumina under conditions as indicated in Table 2. In Example 22, 6.2 grams of ferric chloride and 9.6 grams of pyridine were used, respectively. In Example 23, the formula PdCl$_2$(py)$_2$ indicates a palladium chloride-pyridine complex. The results were as shown in Table 2. In all of these examples, the degree of corrosion was as small as below 0.05 mm./year or no corrosion was observed. The diurethane was obtained at high yield in these examples.

Table 2

| Example No. | Primal catalyst Kind | Amount (g) | Reaction time (min.) | Yield (%) Mononitro- monourethane | diurethane |
|---|---|---|---|---|---|
| 20 | 5% Pd on carbon | 1.56 | 150 | 2 | 88 |

Table 2-continued

| Example No. | Primal catalyst Kind | Primal catalyst Amount (g) | Reaction time (min.) | Yield (%) Mononitro-monourethane | Yield (%) diurethane |
|---|---|---|---|---|---|
| 21 | PdCl$_2$ | 0.12 | 120 | 3 | 92 |
| 22 | PdCl$_2$ | 0.02 | 150 | 3 | 92 |
| 23 | PdCl$_2$(py)$_2$ | 0.05 | 120 | 0 | 93 |

EXAMPLE 24

Example 12 was repeated using 15.2 grams of a ferric chloride-pyridine complex instead of 4.2 grams of ferric chloride and 6.3 grams of pyridine. Similar results were obtained and the yield of the diurethane was 95%.

EXAMPLE 25

Example 12 was repeated using 18.2 grams of 2,6-dinitrotoluene instead of 18.2 grams of 2,4-dinitrotoluene. 180 Minutes after commencement of the reaction, the diurethane (i.e., diethyltoluene-2,6-dicarbamate) was obtained at a yield of 92%.

EXAMPLE 26

Example 12 was repeated using 18.2 grams of a dinitrotoluene mixture of 2,4-dinitrotoluene and 2,6-dinitrotoluene in a ratio of 80:20 instead of 18.2 grams of 2,4-dinitrotoluene. 180 Minutes after commencement of the reaction, the diurethane was obtained at a yield of 95%. The diurethane had a 2,4-compound to 2,6-compound ratio of about 80:20.

EXAMPLE 27

Example 21 was repeated using 0.20 grams of ruthenium chloride instead of 0.12 gram of palladium chloride. 180 Minutes after commencement of the reaction, there were obtained mononitromonourethane at a yield of 14% and diurethane at a yield of 76%, respectively.

EXAMPLE 28

Example 27 was repeated using 0.3 gram of rhodium chloride instead of 0.20 gram of ruthenium chloride. Similar results were obtained.

EXAMPLE 29

18.2 Grams of 2,4-dinitrotoluene, 150 ml. of ethanol, 1.56 grams of 5% palladium on carbon, 4.2 grams of ferric chloride and 6.3 grams of pyridine were placed in a 500 ml. autoclave. The air in the system was replaced by nitrogen gas and carbon monoxide was fed into the autoclave in such a manner that the initial pressure reached 70 kg/cm$^2$G. Then, the content was heated up to 160° C. while agitating and maintained at that temperature for 150 minutes for reaction, so that no drop in pressure was observed and thus the reaction was completed. The autoclave was cooled down to 60° C. and the gases were exhausted therefrom. The reaction solution was subjected to filtration at 60° C. for removal of solids therefrom to recover 10.1 grams of the catalyst. The resultant filtrate was further cooled to room temperature for crystallization of the urethane product, which was separated by filtration, followed by washing with 15 ml. of cool ethanol and drying to obtain 17.3 grams of the product. It was found by the analyses that the product had a purity of 99.0% with regard to the diurethane.

The filtrate obtained after separation of the crystals (herein referred to as reaction mother liquor), the washings obtained after washing the crystals, and the recovered catalyst were reintroduced into the autoclave together with 18.2 grams of 2,4-dinitrotoluene for a second cycle of reaction under an initial carbon monoxide pressure of 70 kg/cm$^2$G at a reaction temperature of 160° C. for 150 minutes. By a procedure similar to the first reaction, there were obtained 9.6 grams of recovered catalyst and 24.0 grams of the diurethane with a purity of 98.0%. Then, the above process was repeated for a total of 16 times using the recovered catalyst and the reaction mother liquor by recirculation. In Table 3 are shown the reaction time, yield and purity of the diurethane product in each cycle of the reaction. In the table, the column headed "Cycle No." indicates the number of repetitions of use of the reaction mother liquid. Since the reaction velocity gradually diminished during the repetitions, 4.2 grams of ferric chloride and 6.3 grams of pyridine were each freshly added to the reaction system in the eighth and thirteenth cycles of the reaction. The filtrate obtained after the last cycle of the reaction was concentrated and evaporated to dryness, to which was added water while agitating. The resultant crystals were separated by filtration, washed with water and dried to obtain the diurethane.

In every cycle of the reaction, the operations of discharge from and introduction into the autoclave were effected in a current of dry nitrogen so as to prevent the starting materials and the reaction solution from absorbing moisture. It was found after completion of the sixteenth cycle of the reaction that the degree of corrosion of the agitating blades was as small as 0.01 mm./year, no pitting being observed on the surfaces thereof.

Table 3

| Exp. No. | Cycle No. | Reaction time (min.) | Diurethane Yield (g.) | Diurethane Yield (%) | Purity (%) |
|---|---|---|---|---|---|
| 29-1 | 0 | 150 | 17.3 | 65.0 | 99.0 |
| 29-2 | 1 | 150 | 24.0 | 90.0 | 98.0 |
| 29-3 | 2 | 140 | 24.0 | 90.3 | 98.0 |
| 29-4 | 3 | 190 | 25.4 | 95.6 | 97.5 |
| 29-5 | 4 | 300 | 28.1 | 105.8 | 97.0 |
| 29-6 | 5 | 310 | 22.4 | 84.3 | 99.0 |
| 29-7 | 6 | 300 | 22.3 | 83.9 | 97.2 |
| 29-8[1] | 7 | 360 | 25.3 | 95.2 | 97.8 |
| 29-9 | 8 | 200 | 23.2 | 87.3 | 98.3 |
| 29-10 | 9 | 180 | 24.2 | 91.1 | 98.0 |
| 29-11 | 10 | 220 | 21.3 | 80.2 | 99.0 |
| 29-12 | 11 | 250 | 22.2 | 83.6 | 98.5 |
| 29-13[1] | 12 | 310 | 23.0 | 86.6 | 98.0 |
| 29-14 | 13 | 270 | 25.2 | 94.8 | 97.6 |
| 29-15 | 14 | 260 | 24.1 | 90.7 | 98.0 |
| 29-16 | 15 | 310 | 24.0 | 90.0 | 98.0 |
| 29-16 | Mother Liquor | — | 56.0 | 210.5 | 97.1 |
| | Average | 243 | 24.0 | 90 | 98 |

[1]Addition of ferric chloride and pyridine.

COMPARATIVE EXAMPLE 4

Example 29 was repeated to effect a first reaction without use of pyridine. The reaction was completed 200 minutes after commencement thereof. Only 0.5 gram of catalyst was recovered from the resultant reaction solution in which the ferric chloride was dissolved. The filtrate obtained after separation of the catalyst was cooled to obtain 15.0 grams of diurethane with a purity of 98.0%. The recovered catalyst and the mother liquor were recirculated to the reaction system in the same manner as in Example 29, to which was added fresh 2,4-dinitrotoluene for further reaction. The reaction proceeded so slowly that it took 300 minutes before a drop in pressure was not observed. The catalyst recovered from the resultant reaction solution was as small as 0.5 gram and no diurethane was separated as crystals when the filtrate was cooled at 0° C. over a long period of time. Then, the filtrate was concentrated and evaporated to dryness, to which was added water, followed by agitation to crystallize a reaction product. The crystals were separated by filtration and dried to obtain 23.6 grams of the product. The product was subjected to the analyses and found to be 75% of the diurethane and 20% of the mononitromonourethane. When water was added to the dried material and then agitated, a substantial amount of the product was found to be dissolved in the water. The degree of corrosion of the agitating blades after the two successive reaction operations was as great as 3.0 mm./year, causing a number of pits on the blade surfaces.

COMPARATIVE EXAMPLE 5

Comparative Example 4 was repeated to obtain a second reaction solution. To the reaction solution from which neither catalyst nor diurethane was separated were further added 18.2 grams of 2,4-dinitrotoluene and 15 ml. of ethanol for further reaction. However, substantially no drop in pressure was observed at 160° C. revealing that no reaction occurred.

EXAMPLE 30

The recirculation of recovered catalyst and mother liquor was repeated for a total of 10 times in the same manner as in Example 29 using 1.56 grams of 5% palladium on alumina instead of 1.56 grams of 5% palladium on carbon. No fresh catalyst was added to the reaction system during the recirculation test. The average reaction time of these reactions was 200 minutes, the average yield of diurethane was 95%, and the average purity was 98%.

EXAMPLE 31

18.2 Grams of 2,4-dinitrotoluene, 0.025 gram of palladium chloride, 4.2 grams of ferric chloride, 6.3 grams of pyridine and 150 ml. of ethanol were used for reaction in the same manner as in Example 29. The recovered catalyst and mother liquor obtained from the resultant reaction solution were reused several times by recirculation. The reaction time, yield and purity of the diurethane in each test are shown in Table 4 below wherein the column headed "Cycle No." again indicates the number of repetitions of use of the reaction mother liquor. During the test, the reaction velocity became so slow that 4.2 grams of ferric chloride and 6.3 grams of pyridine were freshly added to the reaction system in the third cycle thereof.

Table 4

| Exp. No. | Cycle No. | Reaction time (min.) | Diurethane Yield (g.) | Yield (%) | Purity (%) |
|---|---|---|---|---|---|
| 31-1 | 0 | 290 | 17.1 | 63.9 | 99.7 |
| 31-2 | 1 | 310 | 24.5 | 91.5 | 99.0 |
| 31-3[1] | 2 | 150 | 23.4 | 88.0 | 98.0 |
| 31-4 | 3 | 190 | 25.4 | 95.5 | 99.5 |
| 31-5 | 4 | 210 | 24.7 | 92.6 | 97.8 |
| 31-5 | Mother Liquor | — | 11.7 | 44.1 | 99.0 |
|  | Average | 230 | 25.4 | 95.1 | 98.8 |

[1]Addition of ferric chloride and pyridine.

EXAMPLE 32

Example 31 was repeated using 15.2 grams of a ferric chloride-pyridine complex and 0.125 gram of palladium chloride instead of 4.2 grams of ferric chloride, 6.3 grams of pyridine and 0.025 gram of palladium chloride, for the recirculation test using recovered catalyst and mother liquor. No fresh catalyst was added to the reaction system during the test. The average reaction time of five cycles was 150 minutes, the average yields by amount and percentage were 25.3 grams and 95%, respectively, and the average purity was 99%.

EXAMPLE 33

Example 31 was repeated using 10.3 grams of isoquinoline instead of 6.3 grams of pyridine for effecting the recirculation test using recovered catalyst and mother liquor. Results similar to those of Example 31 were obtained.

EXAMPLE 34

Example 32 was repeated using 0.2 gram of ruthenium chloride instead of 0.025 gram of palladium chloride for effecting the recirculation test using recovered catalyst and mother liquor. As a result, the average reaction time was 180 minutes, the average yield of diurethane was 21.3 grams, i.e., the average yield by percentage was 80%, and the average purity was 98%.

EXAMPLE 35

Example 34 was repeated using 0.3 gram of rhodium chloride instead of 0.2 gram of ruthenium chloride for effecting the recirculation test using recovered catalyst and mother liquor. Results similar to those of Example 34 were obtained.

EXAMPLE 36

12.3 Grams of nitrobenzene, 0.78 gram of 5% palladium on alumina, 4.0 grams of ferric chloride, 6.0 grams of pyridine and 150 ml. of ethanol were placed in a 500 ml. autoclave. The air in the autoclave was replaced by nitrogen gas and then carbon monoxide was fed into the autoclave until its initial pressure reached 50 kg/cm$^2$G. The content was heated with agitation for reaction at a temperature of 150°-160° C. for 30 minutes. After completion of the reaction, the reaction system was cooled and the gases in the system were exhausted from the autoclave. The insoluble materials were separated from the reaction solution by filtration to obtain 9.0 grams of solids which were subjected to analysis by an atomic absorption spectroscopy. As a result, it was found that 85% of the charged catalyst was recovered. Then, the ethanol was removed from the resultant filtrate by distillation to obtain the reaction product. It was found by chromatographic analyses that the product contained no unreacted nitrobenzene and that the yield of the urethane, i.e., N-phenylcarbamic acid ethyl ester, was 97%. The degree of corrosion of the agitating blades was as small as 0.003 mm./year, no change being observed on surfaces of the blades.

COMPARATIVE EXAMPLE 6

Example 36 was repeated without use of pyridine at a reaction temperature of 150° C. 60 Minutes after commencement of the reaction, the reaction was completed. Analyses of the resultant product revealed that no starting nitrobenzene was detected and that the yield of the urethane was 85%. The degree of corrosion of the agitating blades was as great as 1.5 mm./year, a number of pittings being observed on the surfaces of the blades. The recovery percentage of the catalyst was only 15%.

EXAMPLE 37

Example 36 was repeated using 13.7 grams of p-nitrotoluene instead of 12.3 grams of nitrobenzene and a reaction time of 40 minutes. As a result, the urethane, i.e., N-p-tolylcarbamic acid ethyl ester, was obtained at a yield of 95%. The degree of corrosion was as small as 0.005 mm./year.

What is claimed is:

1. A process for producing an aromatic urethane comprising interacting an aromatic nitro compound selected from the group consisting of nitroaromatic hydrocarbons, halogenated nitroaromatic hydrocarbons and bis (nitrophenyl)ethers, a hydroxyl group-containing organic compound selected from the group consisting of a monohydric alcohol, a polyhydric alcohol, a monohydric phenol and a polyhydric phenol and carbon monoxide in a reactor under an initial carbon monoxide pressure of 10–500 kg/cm$^2$ and a temperature of 80°–260° C. in the presence of a catalyst composed of (1) a member selected from the group consisting of the metals palladium, ruthenium and rhodium and a catalytically active compound thereof selected from the group consisting of the halide, cyanide, thiocyanide, isocyanide, oxide, sulfate, nitrate, and carbonyl compounds of said metals, the complex salt of said halide with a tertiary amine, and the complex salt of said halide with triphenylphosphine, (2) a Lewis acid, and (3) a tertiary amine which suppresses corrosion of the reactor material by the Lewis acid and which forms an insoluble solid with said member and said Lewis acid, the molar ratio of said tertiary amine to the anions of said Lewis acid being in the range of 0.5 to 5.

2. The process according to claim 1 wherein said aromatic nitro compound is dinitrotoluene.

3. The process according to claim 1 wherein said hydroxyl group-containing organic compound is ethyl alcohol.

4. The process according to claim 1 wherein said tertiary amine is a nitrogen-containing heterocyclic tertiary amine.

5. The process according to claim 4 wherein said nitrogen-containing heterocyclic tertiary amine is pyridine.

6. The process according to claim 4 wherein said nitrogen-containing heterocyclic tertiary amine is isoquinoline.

7. The process according to claim 4 including the further steps of separating the insoluble catalyst and crystals of said aromatic urethane from the reaction solution obtained after completion of the reaction and recirculating the resultant reaction mother liquor to the reaction system.

8. The process according to claim 4 including the further steps of separating the insoluble catalyst from the reaction solution obtained after completion of the reaction, cooling the resultant filtrate to separate said aromatic urethane as crystals, and recirculating said insoluble catalyst and the resultant reaction mother liquor to the reaction system.

9. The process according to claim 1, wherein said aromatic nitro compound is dinitrotoluene, said hydroxyl group-containing organic compound is ethyl alcohol, and said tertiary amine is a nitrogen-containing heterocyclic tertiary amine.

* * * * *